(12) United States Patent
Nord et al.

(10) Patent No.: US 9,731,147 B2
(45) Date of Patent: Aug. 15, 2017

(54) METHOD AND APPARATUS PERTAINING TO THE OPTIMIZATION OF RADIATION-TREATMENT PLANS USING AUTOMATIC CHANGES TO TREATMENT OBJECTIVES

(75) Inventors: Janne Nord, Espoo (FI); Juha Kauppinen, Espoo (FI); Lauri Halko, Helsinki (FI); Jarkko Peltola, Tuusula (FI)

(73) Assignee: Varian Medical Systems International AG, Cham (CH)

( * ) Notice: Subject to any disclaimer, the term of this patent is extended or adjusted under 35 U.S.C. 154(b) by 187 days.

(21) Appl. No.: 13/367,620

(22) Filed: Feb. 7, 2012

(65) Prior Publication Data
US 2013/0204067 A1 Aug. 8, 2013

(51) Int. Cl.
*A61N 5/10* (2006.01)
(52) U.S. Cl.
CPC .................. *A61N 5/1038* (2013.01)
(58) Field of Classification Search
CPC .................. A61N 5/1031; A61N 5/107; A61N 5/103–5/1084; A61N 2005/1032–2005/1098
USPC ................................................. 600/1; 378/65
See application file for complete search history.

(56) References Cited

U.S. PATENT DOCUMENTS

2009/0116616 A1* 5/2009 Lu et al. ........................ 378/65
2010/0104068 A1* 4/2010 Kilby ................... A61N 5/1031
378/65
2010/0183121 A1* 7/2010 Riker et al. ..................... 378/65

\* cited by examiner

*Primary Examiner* — Charles A Marmor, II
*Assistant Examiner* — Thaddeus Cox
(74) *Attorney, Agent, or Firm* — Fitch, Even, Tabin & Flannery LLP

(57) ABSTRACT

Optimization of a radiation-delivery treatment plan can be facilitated by permitting the making of automatic changes to one or more treatment objectives. This can comprise processing radiation-delivery treatment plan parameters with respect to one or more predetermined treatment objectives and then automatically changing that predetermined treatment objective to provide one or more changed treatment objectives (including altered, deleted, and/or added treatment objectives) that can then be used to at least attempt to optimize a radiation-delivery treatment plan. That predetermined treatment objective can comprise, for example, a treatment objective as regards a given treatment volume. The automatic changing of the predetermined treatment objective can occur in response to a variety of stimuli such as detecting a change with respect to a treatment condition such as a change in the presentation of a patient volume of interest.

12 Claims, 6 Drawing Sheets

METHOD AND APPARATUS PERTAINING TO THE OPTIMIZATION OF RADIATION-TREATMENT PLANS USING AUTOMATIC CHANGES TO TREATMENT OBJECTIVES

TECHNICAL FIELD

This invention relates generally to radiation-treatment planning.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not discriminate between unwanted structures and adjacent tissues, organs, or the like that are desired or even critical to continued survival of the patient. As a result, radiation is ordinarily applied in a carefully administered manner to at least attempt to restrict the radiation to a given target volume.

Such plans are often calculated using an iterative process. Beginning with some initial set of parameter settings, a radiation-treatment planning apparatus iteratively adjusts one or more of those settings and assesses the relative worth of the adjusted plan. An iterative approach such as this is often referred to as "optimizing" the plan (where "optimizing" should not be confused with the idea of identifying an objectively "optimum" plan that is superior to all other possible plans).

Optimizing such a plan can prove challenging as the overall computational requirements can be considerable. As one example in these regards, such a candidate treatment plan often comprises a plurality of control points (pertaining, for example, to collimator leaf settings at each of a plurality of source angles in an arc therapy application setting). In some application settings, the time required to work through such iterative calculations can result in vexing delays. These delays, in turn, can lead to expensive and undesirable equipment downtime, patient discomfort, and increased costs.

Furthermore, many existing radiation treatment-planning approaches require considerable interaction with an expert technician, physician, or the like. For example, good plans typically require adaptation of optimization objectives (which describe the end results being sought via administration of the radiation treatment) according to patient geometry per a skilled-person's input. To put this another way, it has not been ordinarily possible to simply specify optimization objectives for radiation-treatment plan optimization regardless of the individual patient's respective and relevant geometry (and/or regardless of how a patient's geometry may change over time) as existing approaches will not support such an approach. The resultant required interaction with a skilled user, in turn, leads to increased cycle-time requirements and a corresponding burden upon the user. Beyond this, such demands upon the availability of skilled planners can ultimately affect the performance of an entire medical-treatment facility and hence the overall quality of treatment across a significant patient population.

BRIEF DESCRIPTION OF THE DRAWINGS

The above needs are at least partially met through provision of the method and apparatus pertaining to the optimization of radiation-treatment plans using automatic changes to treatment objectives described in the following detailed description, particularly when studied in conjunction with the drawings, wherein.

Figure 1:
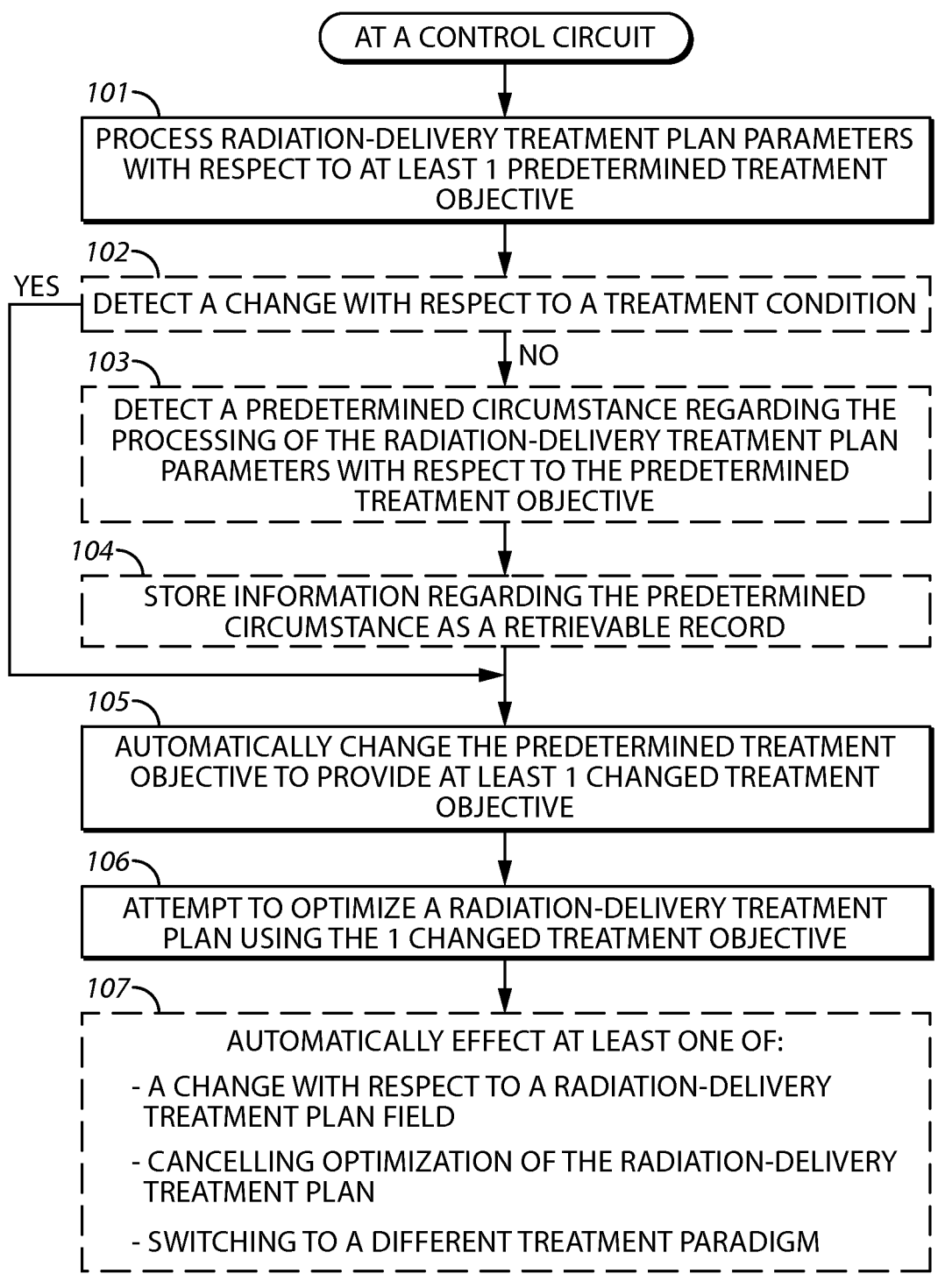
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, optimization of a radiation-delivery treatment plan can be facilitated, at least in part, by permitting the process to make automatic changes to one or more treatment objectives. This can comprise, for example, processing radiation-delivery treatment plan parameters with respect to one or more predetermined treatment objectives and then automatically changing that predetermined treatment objective to provide one or more changed treatment objectives that can then be used to at least attempt to optimize a radiation-delivery treatment plan.

By one approach, that predetermined treatment objective can comprise, for example, a treatment objective as regards a given treatment volume. Such a treatment objective might comprise, by way of illustration, a dose volume histogram objective. By one approach, that changed treatment objective can comprise, at least in part, a changed treatment region.

The aforementioned automatic changing of the predetermined treatment objective can occur in response to a variety of stimuli. By one approach, for example, this change can comprise a response to detecting a change with respect to a treatment condition such as a change in the presentation of a patient volume of interest (such as a treatment target and/or adjacent tissue/organs to be protected).

These teachings are highly flexible in practice and will accommodate a considerable range of variations and alterations. By one approach, for example, these teachings can include detecting a predetermined circumstance regarding the processing of the radiation-delivery treatment plan parameters with respect to the aforementioned predetermined treatment objective. In this case, the automatic changing of the predetermined treatment objective can comprise a response to detecting this predetermined circumstance. These teachings will accommodate a wide range of predetermined circumstances including, but not limited to, a failure to achieve the predetermined treatment objective within a given period of time, achieving the predetermined treatment objective within a given period of time, completing a predetermined number of optimization iterations, failing to improve a processing result notwithstanding improvement attempts, and so forth.

Approaches such as these permit optimization of a radiation-delivery treatment plan to occur with greater autonomy and a decreased reliance upon real-time (including near real-time) expert interaction. These approaches can also be readily leveraged to facilitate building improved automated responses and adjustments to thereby even further reduce the need for real-time monitoring, inputs, and interaction by one or more skilled users. These teachings can also lead to specific or general improvement in the quality of treatment plans, for example, by reducing the dosing of critical organs while increasing the dosing of intended targets, by helping to reduce risks associated with human error, and so forth.

These and other benefits may become clearer upon making a thorough review and study of the following detailed description. Referring now to the drawings, and in particular to FIG. 1, an illustrative process 100 that is compatible with many of these teachings will now be presented. For the sake of illustration it will be presumed that a control circuit of choice carries out this process 100 with further exemplary details in those regards appearing further below.

Figure 2:
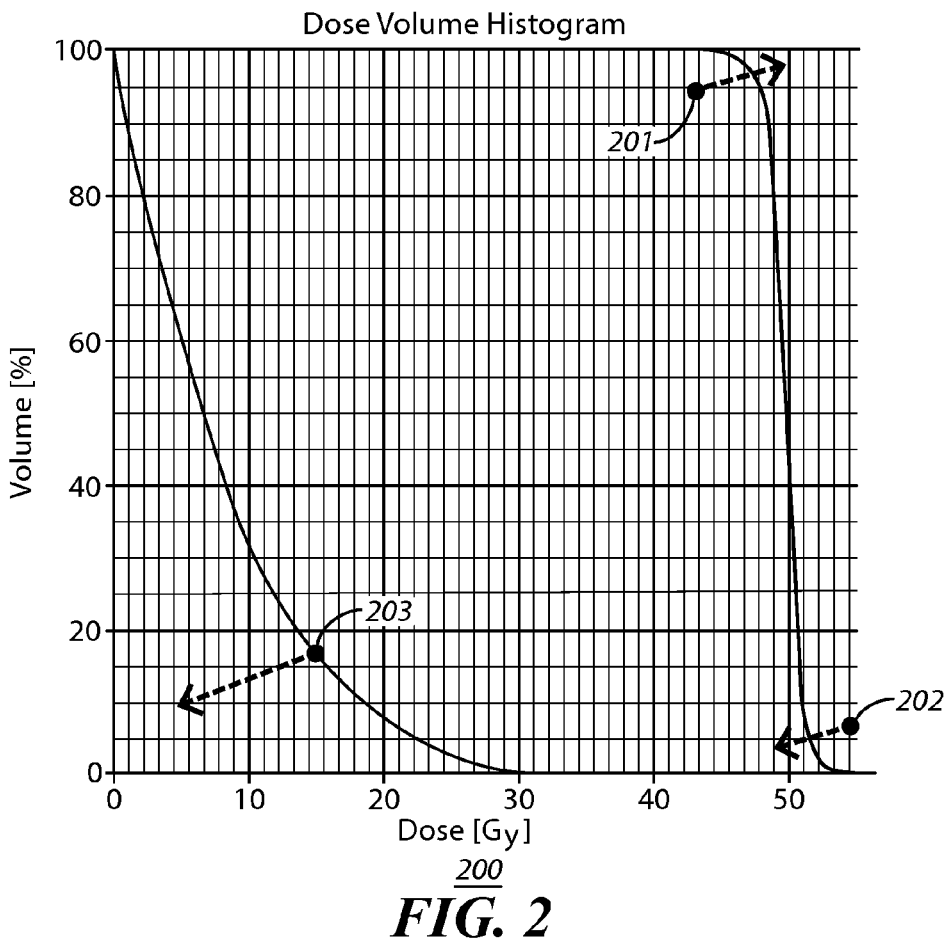
FIG. 2 comprises a graph as configured in accordance with various embodiments of the invention.

Step 101 provides for processing radiation-delivery treatment plan parameters with respect to at least one predetermined treatment objective. This process 100 will accommodate any of a variety of radiation-delivery treatment plan parameters. As one non-limiting example in these regards, the predetermined treatment objective can comprise a treatment objective as regards a given treatment volume. This given treatment volume can comprise, for example, the general area within the patient that includes the treatment target and can include any of a patient's target volume (i.e., the volume to be intentionally dosed in order to treat a condition within this volume), a critical volume (i.e., a volume for which dosing is to be avoided to an extent possible), and a secondary volume (i.e., a volume that is not a specific treatment target but is also not specifically identified as meriting dosing avoidance to a same extent as a critical volume). This can include dose volume histogram (DVH) objectives. FIG. 2 provides an illustrative example of a DVH 200.

DVH's typically represent three-dimensional dose distributions in a graphical two-dimensional format (the three-dimensional dose distributions being created, for example, in a computerized radiation-treatment planning system based on a three-dimensional reconstruction of an X-ray computed tomography scan and study. The "volume" referred to in DVH analysis can be, for example, the radiation-treatment target, a healthy organ located near such a target, an arbitrary structure, and so forth.

DVH's are often visualized in either of two ways: as differential DVH's or as cumulative DVH's. With differential DVH's column height for a given dose bin corresponds to the volume of the structure that receives that dose. Bin doses typically extend along the horizontal axis while structure volumes (either percent or absolute volumes) extend along the vertical axis.

A cumulative DVH is typically plotted with bin doses along the horizontal axis but has a column height for the first bin that represents the volume of structure(s) that receive greater than or equal to that dose. The column height of the second bin then represents the volume of structure(s) that receive greater than or equal to that dose, and so forth. With high granularity a cumulative DVH often appears as a smooth line graph. For many application settings cumulative DVH's are preferred over differential DVH's but this process 100 can accommodate either approach.

Figure 3:
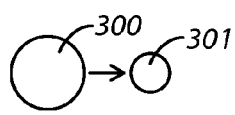
FIG. 3 comprises a schematic representation as configured in accordance with various embodiments of the invention.
Figure 4:
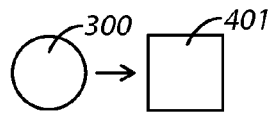
FIG. 4 comprises a schematic representation as configured in accordance with various embodiments of the invention.
Figure 5:
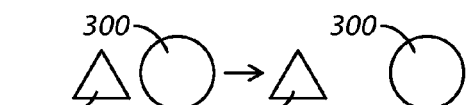
FIG. 5 comprises a schematic representation as configured in accordance with various embodiments of the invention.

Referring again to FIG. 1, optional step 102 provides for detecting a change with respect to one or more treatment conditions. This can comprise, for example, a change with respect to the presentation of one or more patient volumes of interest. Without intending any particular limitations in these regards, FIG. 3 illustrates that this change can comprise, for example, a change with respect to the size of a patient volume as when the original volume 300 shrinks to a smaller-sized volume 301. As another example, FIG. 4 illustrates that this change can comprise a change with respect to the shape of a patient volume as when the original volume 300 having a first shape assumes a second, different shape 401. And as yet another example, FIG. 5 illustrates that this change can comprise a change with respect to a relative position of the patient volume as when the patient volume 300 has an original relative position with respect to another object 501 (such as an organ to be protected) and the relative distance between these two objects 300 and 501 increases. Numerous other possible changes (including combinations of the foregoing) are of course possible and can constitute the "change" contemplated herein.

Such a change can be detected, for example, by comparing images (such as but not limited to X-ray images) for the patient that were captured at different points in time. Such comparisons can be automatically effected if desired. This ability to compare images is known in the art and hence will not be described here in greater detail.

This detection of a change comprises a flexible concept in practice and can include, for example, making an observation based upon a model of a treatment where the geometry can be different between an actual patient and a reference patient (i.e., a real other patient or a so-called atlas patient). In such a case, this difference can, in and of itself, comprise a "change" for the purposes of this process 100.

It will therefore be understood that this "treatment condition" can, as desired, include past, present, future, and other sets of detectable information or conditions, in addition to the treatment plan being optimized. Similar to the treatment plan being optimized, such information/conditions can comprise, for example, physical and/or biological dose distribution accumulations in a given patient. As another example, such information/conditions can comprise or otherwise represent a delivered treatment, a future treatment, or even a treatment that is delivered at least partially in parallel with the treatment being optimized (i.e., a treatment that is not literally or specifically in the scope of the optimization process itself (such as, for example, a model is what is often called the "base dose," which is a dose distribution summed to the optimization dose and hence affects the planned dose being optimized while itself remaining unchanged throughout the optimization)).

This detection of a change with respect to one or more treatment conditions effectively facilitates observation of the dose distribution in relation to various patient regions of interest during optimization. The dose distribution can include and/or otherwise account for both plan-based dosing (per the plan being optimized) as well as dosing-related observations or concerns that are otherwise attributable.

With continued reference to FIG. 1, upon detecting such a change this process 100 provides at step 105 for automatically changing the predetermined treatment objective to provide at least one changed treatment objective. As illustrated in FIG. 2, when the treatment objective(s) comprises a DVH-based treatment objective this can comprise changing one or more of those DVH-based treatment objectives as represented here by the changed objectives denoted by reference numerals 201, 202, and 203.

As another example in these regards, this change can comprise changing the predetermined treatment objective, at least in part, by changing a treatment region (such as a target region to be dosed), a critical region (such as important organs and tissues that are not to be dosed), or such other region as may be appropriate. As one simple example in such regards, this could comprise changing a three-dimensional margin for an organ from 2.0 centimeters to 1.0 centimeters or to 3.0 centimeters.

Generally speaking, this process 100 will accommodate deleting or changing any existing treatment objective as well as adding other, new treatment objectives (to supplement or to substitute for an existing treatment objective as appropriate). This process 100 can also accommodate, if desired, regions that do not have a specific treatment objective (where, for example, such regions can serve to facilitate evaluating dosing per the optimization procedure). For example, the boundaries, placement, and/or treatment of such regions can be changed by the optimization procedure notwithstanding a lack of a specific treatment objective as regards such regions.

This process 100 will also accommodate other approaches in these regards, including a change to the treatment approach itself (for example, from one kind of radiation-based treatment modality to another) and/or to substituting a completely different set of treatment objectives for those originally specified. This step 105 can also comprise, if desired, initiating a new optimization process (to replace the current optimization process or as a supplemental, parallel process). In such a case this process 100 can then provide for comparing the respective results from a plurality of such processes in order to identify a most-effective treatment plan.

By one approach the changes can be previously specified, both in type and in degree. Using this approach this process 100 can seek to leverage previously-garnered expert input and/or the beneficial results of previous efforts and processing. By another approach the nature of the change (either in type or in degree) can be automatically selected. If desired, these teachings will accommodate using artificial-intelligence techniques to permit the process 100 to test various automated changes over time and to identify, recall, and reuse changes that yield beneficial results.

In any event, at step 106 this process 100 then attempts to optimize a radiation-delivery treatment plan using that changed treatment objective. In a typical case this will comprise processing one or more iterations of the optimization process (with the word "attempt" serving to denote that a given change to a given treatment objective may possibly be such that it may not be possible to effect such an iteration).

Depending upon the results of the foregoing, an optional step 107 permits the control circuit to automatically effect one or more actions of choice. As non-limiting illustrative examples, these actions can include making a change with respect to a radiation-delivery treatment plan field, cancelling optimization of the radiation-delivery treatment plan, switching to a different treatment paradigm, and so forth. Such actions may be appropriate, for example, when the optimization activity appears fruitless, ill-suited, or too consumptive of time. At least some of these actions may be appropriate, however, even when the optimization process yields useful results. In such a case, for example, making further changes or switching to a different approach can yield further results that can be compared with the earlier-achieved results in order to permit a comparison.

These teachings are highly flexible in these regards and will accommodate a wide variety of automatically-effected actions. Examples include, but are not limited to, changing dose-per-fraction values, dose normalization methods and parameters, the selection of one or more patient images and/or structure sets (pertaining, for example, to one or more patient regions), the selection of one or more target structures, patient orientation during treatment, patient set-up instructions or conditions, the scheduling of treatment, imaging, and/or other patient appointments, and even such things as the information content to be displayed regarding the treatment plan, relevant regions, and so forth.

As described above, this process 100 provides for automatically changing (at step 105) a predetermined treatment objective in response to detecting (at step 102) a change with respect to a treatment condition. This process 100 will readily accommodate other approaches in these regards, however. As another non-limiting illustrative example in these regards, at optional step 103 the control circuit can detect a predetermined circumstance regarding the processing of the radiation-delivery treatment plan parameters with respect to the aforementioned predetermined treatment objective(s). In this case, the step 105 of automatically changing the predetermined treatment object can occur in response to detecting this predetermined circumstance regarding the processing of the radiation-delivery treatment plan parameters.

The specific nature of the predetermined circumstance can of course vary with the needs and/or opportunities as correspond to a given application setting. Illustrative examples of predetermined circumstances include, but are not limited to:
- a failure to achieve the at least one predetermined treatment objective within a given period of time;
- achieving the at least one predetermined treatment objective within a given period of time;
- completing a predetermined number of optimization iterations; and/or
- a failure to improve a processing result notwithstanding improvement attempts (such as those described herein).

If desired, and as a further illustrative example of the flexibility of this process 100, information regarding the foregoing detections and responses can be stored. This stored information can later serve as report content or as data to facilitate automated or tended learning and processing improvements. As a simple illustrative example in such regards, at optional step 104 this process 100 provides for storing the aforementioned information regarding the predetermined circumstance(s) as a retrievable record. This can comprise locally storing this information and/or remotely storing this information as desired.

So configured, this process 100 will permit a radiation-delivery treatment plan optimization process to proceed in the absence of (or with greatly-reduced reliance upon) real-time end-user interaction. Instead, as treatment circumstances change over time and/or as optimization attempts hit any of a variety of processing milestones this process 100 permits one or more treatment objectives themselves (as versus mere treatment-delivery parameters) to be automatically changed and utilized during continued optimization efforts. This can greatly reduce the total cycle time and cost required to achieve useful results.

Figure 6:
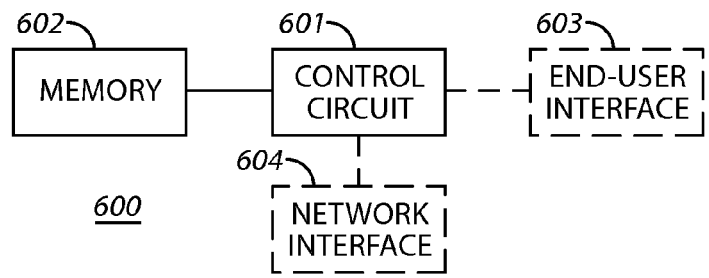
FIG. 6 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 6, an illustrative approach to such a platform will now be provided.

In this example the enabling apparatus 600 includes a control circuit 601 that operably couples to a memory 602. Such a control circuit 601 can comprise a fixed-purpose hard-wired platform or can comprise a partially or wholly programmable platform. These architectural options are well known and understood in the art and require no further description here. This control circuit 601 is configured (for example, by using corresponding programming as will be well understood by those skilled in the art) to carry out one or more of the steps, actions, and/or functions described herein.

The memory 602 may be integral to the control circuit 601 or can be physically discrete (in whole or in part) from the control circuit 601 as desired. This memory 602 can also be local with respect to the control circuit 601 (where, for example, both share a common circuit board, chassis, power supply, and/or housing) or can be partially or wholly remote with respect to the control circuit 601 (where, for example, the memory 602 is physically located in another facility, metropolitan area, or even country as compared to the control circuit 601).

This memory 602 can serve, for example, to non-transitorily store the computer instructions that, when executed by the control circuit 601, cause the control circuit 601 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

As desired, this apparatus 600 can further comprise an end-user interface 603 (such as any of a variety of user-input mechanisms (such as keyboards, cursor-control devices, touch-sensitive displays, and so forth) and user-output mechanisms (such as displays, printers, audio transducers, and so forth) and/or a network interface 604 (such as a wireless and/or a non-wireless data interface) as desired. Such components can facilitate receiving and providing data, instructions, and other content.

Such an apparatus 600 may be comprised of a plurality of physically distinct elements as is suggested by the illustration shown in FIG. 6. It is also possible, however, to view this illustration as comprising a logical view, in which case one or more of these elements can be enabled and realized via a shared platform. It will also be understood that such a shared platform may comprise a wholly or at least partially programmable platform as are known in the art.

For the sake of illustration and without intending any particular limitations by way of described specificity, a number of implementation examples will now be presented.

EXAMPLE 1

Figure 7:
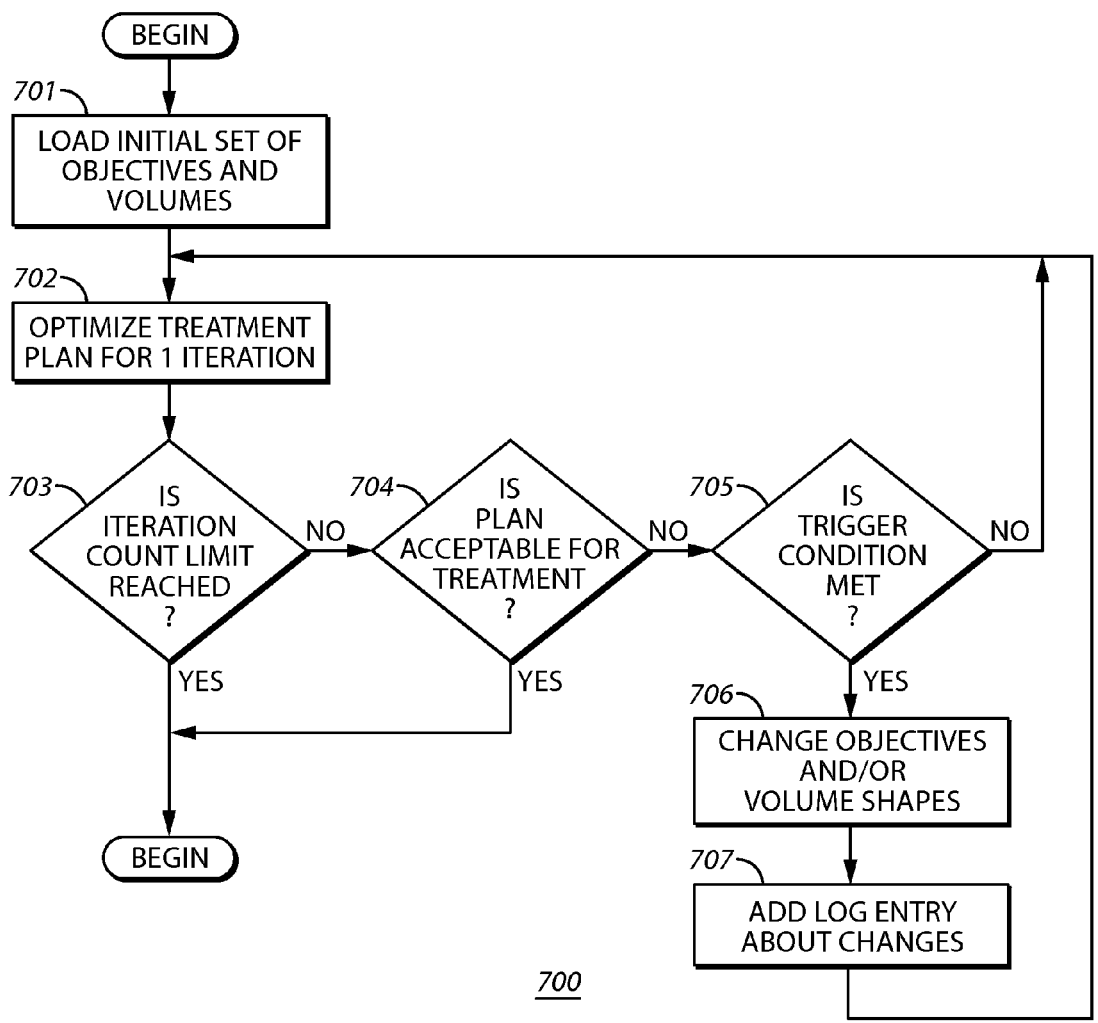
FIG. 7 comprises a flow diagram as configured in accordance with various embodiments of the invention.

With reference to FIG. 7, a radiation-delivery treatment plan optimizer loads 701 an initial set of treatment objectives and corresponding volumes (including, for example, both volumes to be treated and volumes to be protected). The optimizer then iterates 702 the optimization of the radiation-delivery treatment plan and assesses 703 whether a predetermined iteration count limit is met. When "true," the optimization process concludes. Otherwise, the optimizer assesses 704 whether the present resultant radiation-delivery treatment plan is acceptable for treatment (which can comprise, for example, determining whether the current version of the radiation-delivery treatment plan meets all of the specified treatment objectives). If "true," the optimization process can end.

When not "true," however, the optimizer next determines 705 whether a given trigger condition is met. This might comprise, for example, determining whether a treatment condition has changed. If not "true," the optimizer simply again iterates 702 the optimization process and carries on as described above. If "true," however, the optimizer makes 706 appropriate changes (for example, to the treatment objectives and/or to volume shapes) and logs 707 information regarding those changes for future reference and retrieval. The optimization process then continues with further iterations albeit using these changed objectives/shapes.

EXAMPLE 2

Figure 8:
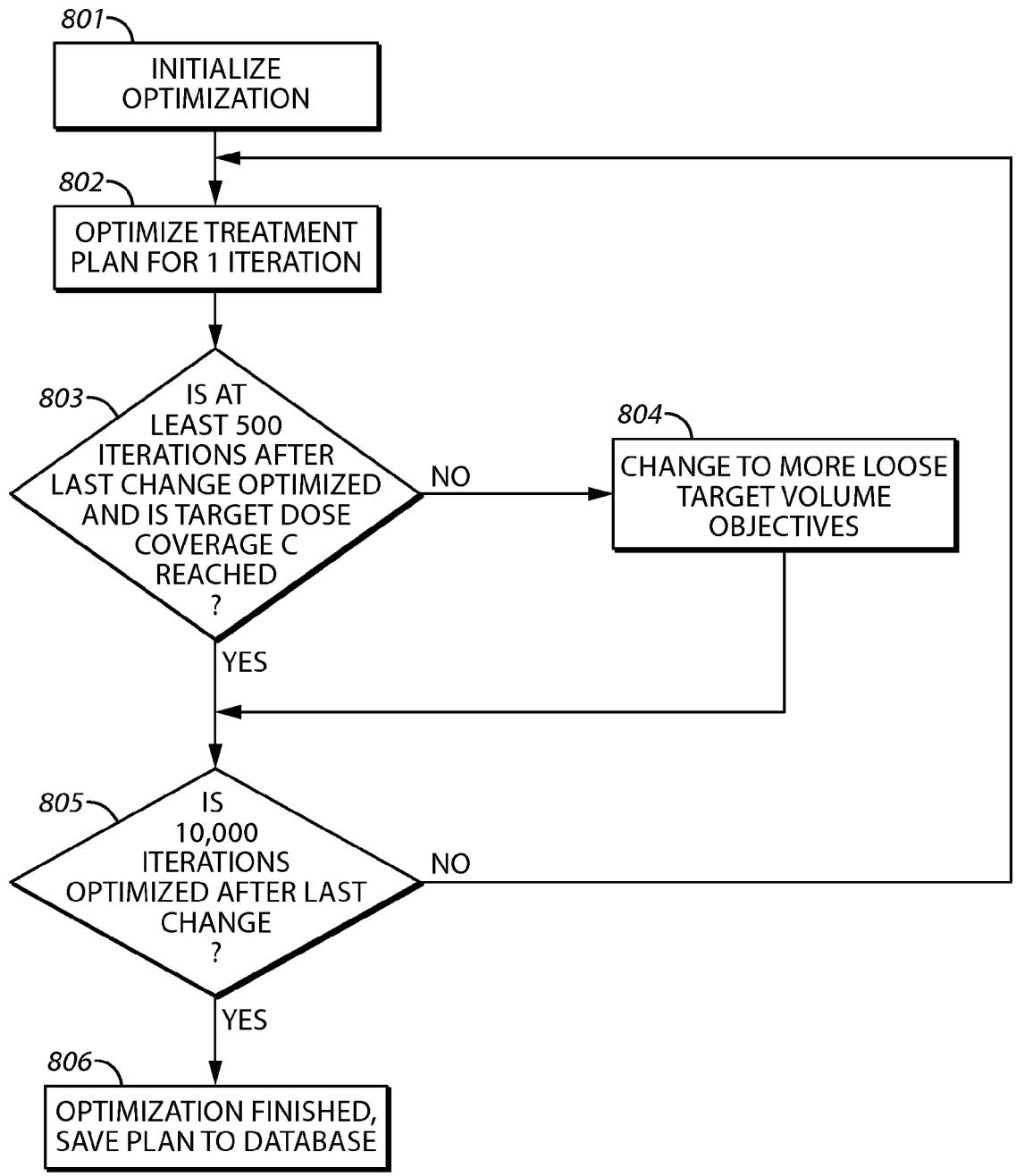
FIG. 8 comprises a flow diagram as configured in accordance with various embodiments of the invention.

With reference to FIG. 8, in this illustrative example the optimizer initializes 801 optimization and conducts 802 an optimization iteration. The optimizer then assess 803 whether it has conducted at least 500 iterations following a last automated change per the foregoing and whether a specified target dose coverage has been attained. When the optimizer has conducted those 500 iterations but without optimization success, the optimizer changes 804 to treatment objectives to specify looser target volume objectives.

Per this illustrative example the optimizer then assesses 805 whether ten thousand optimization iterations have passed since a last such change and, when "true," the optimizer concludes the optimization process and saves the current radiation-delivery treatment plan in a suitable database.

EXAMPLE 3

Figure 9:
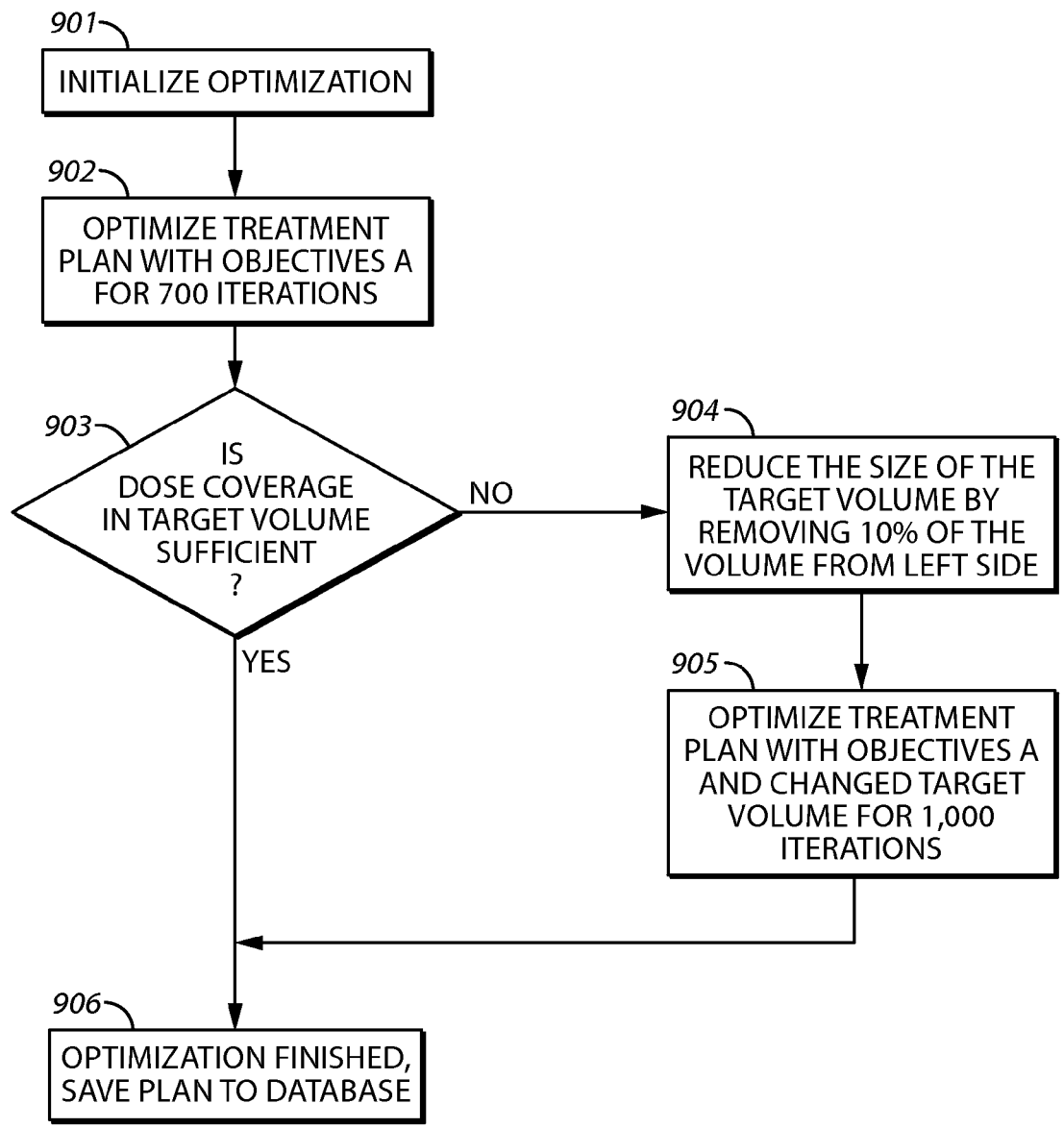
FIG. 9 comprises a flow diagram as configured in accordance with various embodiments of the invention.

With reference to FIG. 9, in this illustrative example the optimizer initializes 901 and works to optimize 902 a radiation-delivery treatment plan having objective A using 700 optimization iterations. The optimizer then assesses 903 the sufficiency of dose coverage in the target volume. When sufficient, the optimizer finishes 906 the optimization process and saves the plan to a database. With insufficient dose coverage, however, the optimizer automatically reduces 904 the size of the target volume by removing ten percent of the volume from the left side thereof and then optimizes 905 (for one thousand additional iterations) the radiation-delivery treatment plan using the same original treatment objective A but changed target volume information.

EXAMPLE 4

Figure 10:
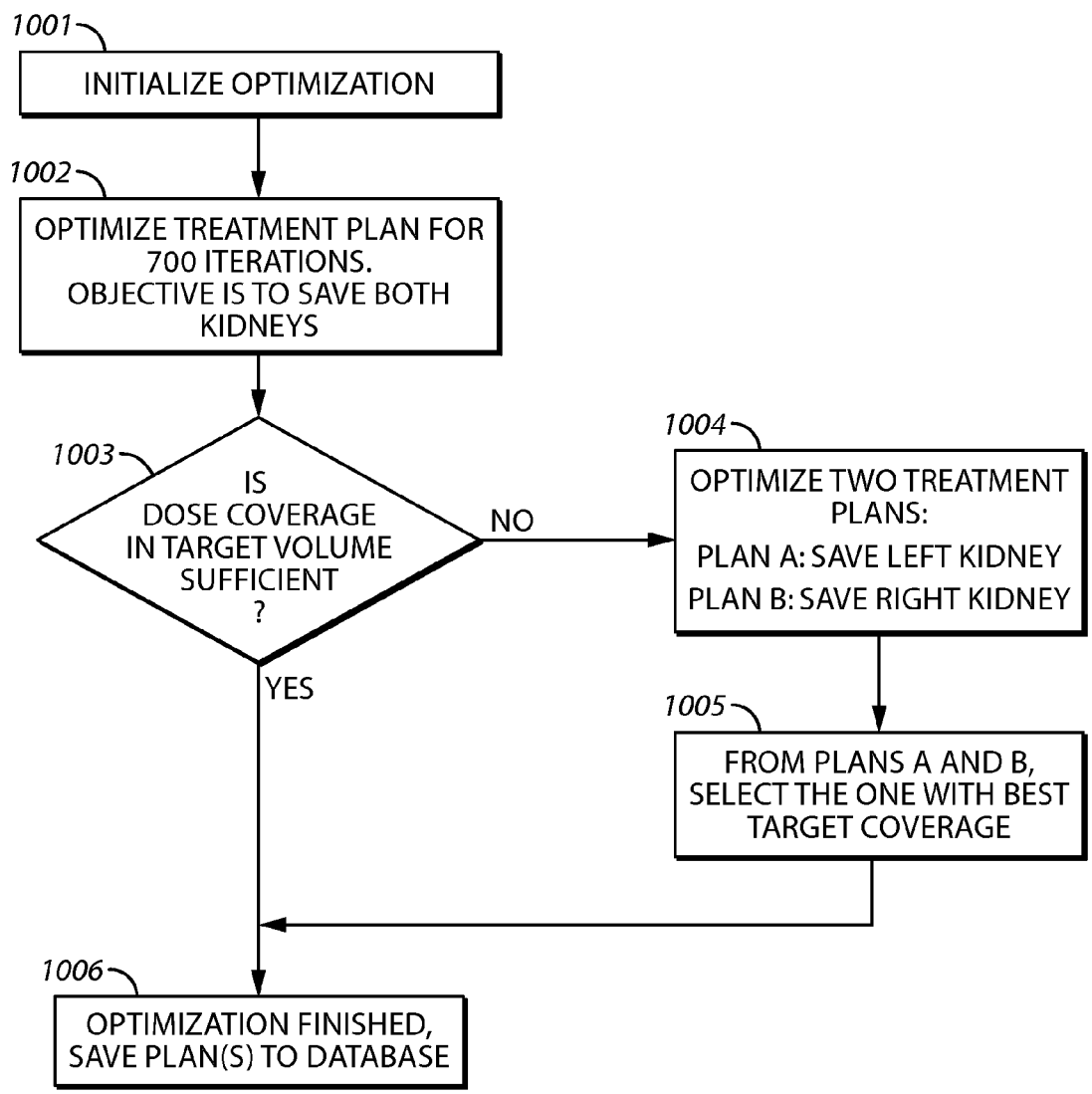
FIG. 10 comprises a flow diagram as configured in accordance with various embodiments of the invention.

With reference to FIG. 10, in this illustrative example the optimizer initializes 1001 and optimizes 1002 the radiation-delivery treatment plan for seven hundred iterations while observing the treatment objective of "saving" both of the patient's kidneys from radiation exposure. Upon concluding those seven hundred iterations the optimizer assesses 1003 the sufficiency of the dose coverage in the target volume. If sufficient, the optimizer finishes 1006 the optimization process and saves the plan to a database.

With insufficient results, however, the optimizer switches to working two different radiation-delivery treatment plans; a plan A that emphasizes saving the patient's left kidney and a plan B that emphasizes saving the patient's right kidney. Optimization of these two plans using these changed treatment objectives can occur one after the other or in parallel as desired. The optimizer then compares 1005 the optimization results for both of these plans and selects the plan that yields the superior dose coverage of the intended target volume.

EXAMPLE 5

The following example serves to illustrate an application of these teachings in a specific context. This illustrative example presumes that a radiotherapy clinic has a rule set for automatic treatment dose optimization for a particular type of lung cancer. A new patient with this lung cancer type enters the clinic and the clinic acquires a computed tomography (CT) image of the patient. A physician delineates the tumor volume and some other relevant volumes of interest in the CT image.

The clinic then uses a treatment planning system to develop a treatment plan for this patient. The system displays a list of available rule sets and a user selects a particular rule set based on the lung cancer type of the patient. The system reads the selected rule set and performs a corresponding treatment planning procedure based on the selected rule set.

In addition, the system reads the CT image and itself automatically delineates additional volumes (beyond those identified by the aforementioned physican) based on the existing volumes and image data. The system uses some of these additional volumes as optimization volumes and uses others of these additional volumes as evaluation volumes that are used when making automated decisions during the procedure.

The system determines a first set of optimization objectives and then begins optimizing a treatment plan using the first set of optimization objectives. In this example the aforementioned rule set specifies that the optimization shall be run until the process converges in a specified manner (or until a specified number of iterations is reached).

Using the evaluation structure and the rule set, the system determines that the dose in the evaluation structure exceeds a limit defined in the rule set. For this case the rule set defines a second set of optimization objectives to be used in a second optimization. The system therefore starts optimizing a treatment plan using the second set of optimization objectives. In this illustrative example this rule set defines that the optimization shall now be run for 100 iterations.

Using the evaluation structure and the rule set the system now determines that the dose in the evaluation structure is within the prescribed limit. Using information regarding a critical structure, a related optimization objective, and the rule set the system determines that the objective is met. In this case the rule set specifies that the optimization shall now be run with a tightened optimization objective.

The system therefore tightens the optimization objective and this results in a third set of optimization objectives. The system starts optimizing a treatment plan using this third set of optimization objectives. In this example, the rule set defines that this optimization runs for 100 iterations.

Using the evaluation structure and the rule set, the system now determines that the dose in the evaluation structure is within the proscribed limit. The system now determines the acceptability of the treatment plan as defined in the rule set. In this example this includes a comparison of dose-volume values against the optimization objectives and a comparison of dose-volume values against expressions defined in the rule set.

The system now determines that the treatment plan is acceptable and displays it to the user. The user, in turn, evaluates the treatment plan and approves the plan as well. The clinic now provides the treatment to the patient according to the created treatment plan.

The teachings set forth herein can permit an advanced treatment planner to specify a set of reusable optimization objectives for a given clinical case. These teachings will also permit an end user to create optimizes treatment plans that are derived from changed optimization objectives without requiring that end user to specify or approve the changed optimization objectives at the time of making use of the change. This, in turn, can lead to easier and faster treatment adaptation. That said, these teachings will also readily accommodate automatic use of predefined operations in response to a variety of condition-based triggers as well as use of user-specified templates for treatment objectives, the foregoing triggers and conditions, and corresponding operations as desired. When working with templates, of course, these teachings will also readily accommodate a user interface that facilitates the creation and modification of such templates (off-line or during interactive optimization as desired).

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method to facilitate optimizing a radiation-delivery treatment plan, comprising:
   by a control circuit:
   before delivering radiation treatment to a target volume in a patient using a resultant radiation-delivery treatment plan:
   accessing a set of rules that control a radiation-delivery treatment plan optimization process as a function of detected changes to a treatment condition;
   loading initial radiation-delivery treatment plan parameters for the target volume with respect to a least one predetermined treatment objective comprising a dose volume histogram objective for a not-yet developed radiation-delivery treatment plan;
   beginning optimization of a radiation-delivery treatment plan using the initial radiation-delivery treatment plan parameters;

detecting a change with respect to a treatment condition;

prior to concluding optimization of the radiation-delivery treatment plan, using the set of rules to automatically change the predetermined treatment objective in response to detecting the change with respect to the treatment condition to provide at least one changed treatment objective;

using the set of rules to continue to optimize the radiation-delivery treatment plan using the at least one changed treatment objective to provide a resultant radiation-delivery treatment plan;

detecting a predetermined state as regards the optimization of the radiation-delivery treatment plan;

in response to detecting the predetermined state, automatically changing a size of the target volume and continuing to radiation-delivery treatment plan to provide a resultant radiation-delivery treatment plan;

after providing the resultant radiation-delivery treatment plan;

using the resultant radiation-delivery treatment plan to delivery the radiation treatment to the patient.

2. The method of claim 1 wherein the at least one predetermined treatment objective comprises a treatment objective as regards a given treatment volume.

3. The method of claim 2 wherein the given treatment volume comprises at least one of a patient's target volume, a critical volume, and a secondary volume.

4. The method of claim 1 wherein the treatment condition comprises presentation of a patient volume.

5. The method of claim 4 wherein the presentation of the patient volume comprises at least one of:
a size of the patient volume;
a shape of the patient volume;
a relative position of the patient volume.

6. The method of claim 1 further comprising:
at the control circuit:
detecting a predetermined circumstance regarding the processing of the radiation-delivery treatment plan parameters with respect to the at least one predetermined treatment objective;
and wherein automatically changing the predetermined treatment objective to provide the at least one changed treatment objective comprises automatically changing the predetermined treatment objective in response to detecting the predetermined circumstance regarding the processing of the radiation-delivery treatment plan parameters.

7. The method of claim 6 wherein the predetermined circumstance regarding the processing of the radiation-delivery treatment plan parameters comprises at least one of:
a failure to achieve the at least one predetermined treatment objective within a given period of time;
achieving the at least one predetermined treatment objective within a given period of time;
completing a predetermined number of optimization iterations;
a failure to improve a processing result notwithstanding improvement attempts.

8. The method of claim 6 further comprising:
at the control circuit:
storing information regarding the predetermined circumstance as a retrievable record.

9. The method of claim 1 further comprising:
at the control circuit:
automatically effecting at least one of:
a change with respect to a radiation-delivery treatment plan field;
cancelling optimizing the radiation-delivery treatment plan;
switching to a different treatment paradigm.

10. The method of claim 1 wherein automatically changing the predetermined treatment objective to provide at least one changed treatment objective comprises, at least in part, changing a treatment region.

11. The method of claim 1 wherein the predetermined state as regards the optimization of the radiation-delivery treatment plan comprises a predetermined number of optimization iterations having been completed without achieving a dose coverage that is sufficient per the dose volume histogram objective.

12. The method of claim 1 wherein the automatically changing a size of the target volume comprising automatically reducing the size of the target volume.

* * * * *